United States Patent
Patel

(12) 
(10) Patent No.: US 6,288,307 B1
(45) Date of Patent: Sep. 11, 2001

(54) CANOLA CULTIVAR 44A89

(76) Inventor: Jayantilal D. Patel, 21 Bayhampton Cres, Thornhill, Ontario (CA), L4J 7S1

(*) Notice: Subject to any disclaimer, the term of this patent is extended or adjusted under 35 U.S.C. 154(b) by 0 days.

(21) Appl. No.: 09/005,817

(22) Filed: Jan. 12, 1998

(51) Int. Cl.$^7$ ............... A01H 5/00; A01H 5/10; A01H 1/04; A01H 4/00; C12N 5/04

(52) U.S. Cl. ............ 800/306; 800/260; 435/410; 435/430

(58) Field of Search .................. 800/298, 306, 800/260; 435/410, 430

(56) References Cited

PUBLICATIONS

Plant Breeders Rights 96–758, *Brassica napus* 44A89, UPOVROM, 1996.*

Barsby, T.L., "A Rapid and Efficient Alternative Procedure for the Regeneration of Plants from Hypocotyl Protoplasts of *Brassica napus*", *Plant Cell Reports*, (1986) (Abstract) vol. 1.5, p. 101–103.

Chuong, Phan V., "A Simple Culture Method for Brassica Hypototyl Protoplasts", *Plant Cell Reports*, 4:4–6 (1985).

Kartha, K.K., In vitro Plant Formation from Stem Explants of Rape (*Brassica napus cv. Zephyr*), *Physiol Plant.*, 31:217–220 (1974).

Narasimhulu, S.B., "Species Specific Shoot Regeneration Response of Cotyledonary Explants of Brassicas", *Plant Cell Reports*, 7:104–106 (1988).

Swanson, Eric B., Chapter 17, p. 159, "Microspore Culture in Brassica", *Methods in Molecular Biology*, vol. 6, Plant Cell and Tissue Culture, Edt. Jeffrey W. Pollard and John M. Walker, by The Humana Press (1990).

* cited by examiner

*Primary Examiner*—Gary Benzion
*Assistant Examiner*—Melissa L. Kimball
(74) *Attorney, Agent, or Firm*—Pioneer Hi-Bred International, Inc.

(57) ABSTRACT

A canola cultivar designated 44A89, plants and seeds of the 44A89 canola cultivar, methods for producing a canola plant produced by crossing the 44A89 cultivar with itself or with another canola plant, and hybrid canola seeds and plants produced by crossing the 44A89 cultivar with another canola line or plant are provided.

12 Claims, No Drawings

CANOLA CULTIVAR 44A89

FIELD OF THE INVENTION

The invention is in the field of *Brassica napus* breeding (i.e., canola breeding), specifically relating to the inbred canola cultivar designated 44A89.

BACKGROUND OF THE INVENTION

The present invention relates to a new and distinctive rapeseed cultivar designated 44A89 which is the result of years of careful breeding and selection. Since such cultivar is of high quality and possesses a relatively low level of erucic acid in the vegetable oil component and a relatively low level of glucosinolate content in the meal component, it can be termed "canola" in accordance with the terminology commonly used by plant scientists.

The creation of new superior, agronomically sound, and stable high yielding cultivars of many plant types including canola has posed an ongoing challenge to plant breeders. In the practical application of a chosen breeding program, the breeder often initially selects and crosses two or more parental lines, followed by repeated selfing and selection, thereby producing many unique genetic combinations. The breeder can theoretically generate billions of different genetic combinations via crossing, selfing and mutagenesis. However, the breeder commonly has no direct control at the cellular level of the plant. Therefore, two breeders will never independently develop the same line, or even very similar lines, having the same canola traits.

Each year, the plant breeder selects the germplasm to advance to the next generation. This germplasm is grown under unique and different geographical, climatic and soil conditions, and further selections are then made during and at the end of the growing season. The characteristics of the cultivars which are developed are incapable of prediction in advance. This unpredictability is because the selection occurs in unique environments, with no control at the DNA level (using conventional breeding procedures), and with millions of different possible genetic combinations being generated. A breeder of ordinary skill cannot predict in advance the final resulting lines that are to be developed, except possibly in a very gross and general fashion. Even the same breeder is incapable of producing the same cultivar twice by using the same original parents and the same selection techniques. This unpredictability commonly results in the expenditure of large research monies and effort to develop a new and superior canola cultivar.

It is recognized that mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and are repeatedly crossed (backcrossed) to the recurrent parent. The resulting plant is expected to have the attributes of the recurrent parent (e.g., cultivar) and the desirable trait transferred from the donor parent. This approach has been used extensively for breeding disease resistant cultivars of many plant types.

Each breeding program should include a periodic, objective evaluation of the efficiency of the breeding procedure. Evaluation criteria varies depending on the goal and objectives, but should include gain from selection per year based on comparisons to an appropriate standard, the overall value of the advanced breeding lines, and the number of successful cultivars produced per unit of input (e.g., per year, per dollar expended, etc.).

Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines commonly are thoroughly tested and are compared to appropriate standards in environments representative of the commercial target area(s) for three or more years. The best lines are candidates for new commercial cultivars; and those still deficient in a few traits may be used as parents to produce new populations for further selection.

These processes, which lead to the final step of marketing and distribution, usually take from approximately eight to twelve years from the time the first cross is made. Therefore, the development of new cultivars such as that of the present invention is a time-consuming process that requires precise forward planning, efficient use of resources, and a minimum of changes in direction.

A most difficult task is the identification of individuals that are genetically superior, because for most traits the true genotypic value may be masked by other confounding plant traits or environmental factors. One method for identifying a superior plant is to observe its performance relative to other experimental plants and to one or more widely grown standard cultivars. If a single observation is inconclusive, replicated observations provide a better estimate of the genetic worth.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of the breeding method. Pedigree breeding and recurrent selection breeding methods are used to develop cultivars from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \circledR F_2$; $F_2 \circledR F_3$; $F_3 \circledR F_4$; $F_4 \circledR F_5$, etc.

Pedigree breeding is commonly used for the improvement of largely self-pollinating crops such as canola. Two parents that are believed to possess favorable, complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

If desired the haploidy method can be used to extract homogeneous lines.

Proper testing should detect any major faults and establish the level of superiority or improvement over current cultivars. In addition to showing superior performance, there must be a demand for a new cultivar that is compatible with industry standards or which creates a new market. The introduction of a new cultivar commonly will incur additional costs to the seed producer, the grower, the processor and the consumer, for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Currently *Brassica napus* canola is being recognized as an increasingly important oilseed crop and a source of meal in many parts of the world. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

*Brassica napus* canola plants are recognized to commonly be self-fertile with approximately 70 to 90 percent of the seed normally forming as the result of self-pollination. The percentage of cross pollination may be further enhanced when populations of recognized insect pollinators at a given growing site are greater.

SUMMARY OF THE INVENTION

According to the present invention, there is provided a novel *Brassica napus* cultivar designated 44A89. This invention thus relates to the seeds of the 44A89 cultivar, to plants of the 44A89 cultivar, and to methods for producing a canola plant produced by crossing the 44A89 cultivar with itself or another canola line.

DEFINITIONS

In the description and tables which follow a number of terms are used. In order to aid in a clear and consistent understanding of the specification the following definitions and evaluation criteria are provided.

Type. This refers to whether the new cultivar is considered to be primarily a Spring or Winter type of canola.

Ploidy. This refers to whether the number of chromosomes exhibited by the cultivar is diploid or tetraploid.

Cotyledon. A cotyledon is a type of seed leaf; a small leaf contained on a plant embryo. A cotyledon contains the food storage tissues of the seed. The embryo is a small plant contained within a mature seed.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development (mean of 50).

Leaf Color. The leaf blade coloration is observed when at least 6 leaves of the plant are completely developed.

Leaf Attachment to Stem. The presence or absence of clasping where the leaf attaches the stem, and when present the degree thereof are observed.

Leaf Glaucousity. The presence or absence of a fine whitish powdery coating on the surface of the leaves, and the degree thereof when present are observed.

Leaf Lobes. The fully developed upper stem leaves are observed for the presence or absence of leaf lobes when at least 6 leaves of the plant are completely developed.

Number of Leaf Lobes. The frequency of leaf lobes when present is observed when at least 6 leaves of the plant are completely developed.

Leaf Surface. The leaf surface is observed for the presence or absence of wrinkles when at least 6 leaves of the plant are completely developed.

Leaf Dentation. The margins of the upper stem leaves are observed for the presence or absence of indentation or serration, and the degree thereof if present when at least 6 leaves of the plant are completely developed.

Leaf Length. The length of the leaf blades and petioles are observed when at least 6, leaves of the plant are completely developed (mean of 50).

Leaf Width. The width of the leaf blades are observed when at least 6 leaves of the plant are completely developed (mean of 50).

Leaf Margin Hairiness. The leaf margins of the first leaf are observed for the presence or absence of pubescence, and the degree thereof when the plant is at the two leaf-stage.

Leaf Upper Side Hairiness. The upper surfaces of the leaves are observed for the presence or absence of hairiness, and the degree thereof if present when at least 6 of the leaves of the plant are formed.

Leaf Attitude. The disposition of typical leaves with respect to the petiole is observed when at least 6 leaves of the plant are formed.

Leaf Tip Reflexion. The presence or absence of bending of typical leaf tips and the degree thereof, if present are observed at the 6 to 11 leaf-stage.

Leaf Anthocyanin Coloration. The presence or absence of leaf anthocyanin coloration and the degree thereof if present are observed when the plant has reached the 9 to 11 leaf-stage.

Petiole Length. The length of the petioles is observed in a cultivar forming lobed leaves when at least 6 leaves of the plant are completely developed.

Stem Anthocyanin Coloration. The presence or absence of leaf anthocyanin coloration and the intensity thereof if present are observed when the plant has reached the 9 to 11 leaf-stage.

Speed of Root Formation. The typical speed of root formation is observed when the plant has reached the 4 to 11 leaf-stage.

Root Depth in Soil. The typical root depth is observed when the plant has reached at least the 6 leaf-stage.

Root Chlorophyll Coloration. The presence or absence of chlorophyll coloration in the skin at the top of the root is observed when the plant has reached at least the 6 leaf-stage.

Root Anthocyanin Coloration. The presence or absence of anthocyanin coloration in the skin at the top of the root is observed when the plant has reached at least the 6 leaf-stage.

Root Anthocyanin Expression. When anthocyanin coloration is present in skin at the top of the root, it further is observed for the exhibition of a reddish or bluish cast within such coloration when the plant has reached at least the 6 leaf-stage.

Root Anthocyanin Streaking. When anthocyanin coloration is present in the skin at the top of the root, it further is observed for the presence or absence of streaking within such coloration when the plant has reached at least the 6 leaf-stage.

Root Coloration Below Ground. The coloration of the root skin below ground is observed when the plant has reached at least the 6 leaf-stage.

Root Flesh Coloration. The internal coloration of the root flesh is observed when the plant has reached at least the 6 leaf-stage.

Seedling Growth Habit. The growth habit of young seedlings is observed for the presence of a weak (1) or strong (9) rosette character and is expressed on a scale of 1 to 9.

Plant Height. The overall plant height at the end of flowering is observed (mean of 50).

Time of Flowering. A determination is made of the number of days when at least 50 percent of the plants have one or more open buds on a terminal raceme in the year of sowing.

Flower Bud Location. A determination is made whether typical buds are disposed above or below the most recently opened flowers.

Flower Petal Coloration. The coloration of open exposed petals on the first day of flowering is observed.

Petal Length. The lengths of typical petals of fully opened flowers are observed (mean of 50).

Petal Width. The widths of typical petals of fully opened flowers are observed (mean of 50).

Anther Dotting. The level of anther dotting when the flowers are fully opened is observed.

Anther Arrangement. The general disposition of the anthers in typical fully opened flowers is observed.

Pollen Formation. The relative level of pollen formation is observed at the time of dehiscence.

Pod Type. The overall configuration of the silique is observed.

Pod Length. The typical silique length is observed and is expressed on a scale of 1 (short) to 5 (long).

Pod Width. The typical silique width when mature is observed and is expressed on a scale of 1 (narrow) to 5 (wide).

Pedicel Length. The typical length of the silique peduncle when mature is observed and is expressed on a scale of 1 (short) to 5 (long).

Length of Beak. The typical length of the silique beak when mature is observed and is expressed on a scale of 1 (short) to 5 (long).

Pod Anthocyanin Coloration. The presence or absence at maturity of silique anthocyanin coloration, and the degree thereof if present are observed.

Pod Habit. The typical manner in which the silique are borne on the plant at maturity is observed.

Maturity. The number of days from planting to maturity is observed with maturity being defined as the plant stage when pods with seed color change, occuring from green to brown or black, on the bottom third of the pod bearing area of the main stem.

Seeds Per Pod. The average number of seeds per pod is observed (mean of 50).

Seed Size. The weight in grams of 1,000 typical seeds is determined at maturity while such seeds exhibit a moisture content of approximately 5 to 6 percent by weight.

Seed Coat Color. The seed coat color of typical mature seeds is observed.

Seed Coat Mucilage. The presence or absence of mucilage on the seed coat is determined and is expressed on a scale of 1 (absent) to 9 (heavy). During such determination a petri dish is filled to a depth of 0.3 cm. with tap water provided at room temperature. Seeds are added to the petri dish and are immersed in water where they are allowed to stand for five minutes. The contents of the petri dish containing the immersed seeds next is examined under a stereo microscope equipped with transmitted light. The presence of mucilage and the level thereof is observed as the intensity of a halo surrounding each seed.

Oil Content: The typical percentage by weight oil present in the mature whole dried seeds is determined by ISO 10565:1993 Oilseeds Simultaneous determination of oil and water—Pulsed NMR method.

Protein Content: The typical percentage by weight of protein in the oil free meal of the mature whole dried seeds is determined by AOCS Official Method Ba 4e-93 Combustion Method for the Determination of Crude Protein.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun et al. *J. Amer. Oil Chem. Soc.*, 60:1751 to 1754 (1983) which is herein incorporated by reference.

Chlorophyll Content. The typical chlorophyll content of the mature seeds is determined by using methods recommended by the WCC/RRC and is considered to be low if <8 ppm, medium if 8 to 15 ppm, and high if 15 to 30 ppm.

Glucosinolate Content. The total aliphatic glucosinolate content of the meal of the seeds is determined on the moisture free air-dried-oil-free solid meal as measured by the gas liquid chromatography method of the Canadian Grain Commission as is expressed micromoles per gram. Capillary gas chromatography of the trimethylsityl derivatives of extracted and purified desulfoglucosinolates with optimization to obtain optimum indole glucosinolate detection as described in *"Procedures of the Western Canada Canola/Rapeseed Recommending Committee Incorporated for the Evaluation and Recommendation for Registration of Canola/Rapeseed Candidate Cultivars in Western Canada"*.

Resistance to Shattering. Resistance to silique shattering is observed at seed maturity and is expressed on a scale of 1 (poor) to 5 (excellent).

Resistant to Lodging. Resistance to lodging at the maturity and is expressed on a scale of 1 (weak) to 5 (strong).

Frost Tolerance (Spring Type Only). The ability of young plants to withstand late spring frosts at a typical growing area is evaluated and is expressed on a scale of 1 (poor) to 5 (excellent).

Winter Survival (Winter Type Only). The ability to withstand winter temperatures at a typical growing area is evaluated and is expressed on a scale of 1 (poor) to 5 (excellent).

Disease Resistance: Resistant to various diseases is evaluated and is expressed on a scale of 0 (not tested), 1 (susceptible), 2 (low resistance), 3 (moderate resistance), or 4 (high resistance).

Herbicide Resistance: Resistance to various herbicides when applied at standard recommended application rates is expressed on a scale of 1 (resistant), 2 (tolerant), or 3 (susceptible).

DETAILED DESCRIPTION OF THE INVENTION

A canola cultivar needs to be homogenous, homozygous and reproducible to be useful for the production of a commercial crop on a reliable basis. There are a number of analytical methods available to determine the homozygotic and phenotypic stability of a canola cultivar.

The oldest and most traditional method of analysis is the observation of phenotypic traits. The data is usually collected in field experiments over the life of the canola plants to be examined. Phenotypic characteristics most often are observed for traits associated with seed yield, seed oil content, seed protein content, fatty acid composition of oil, glucosinolate content of meal, growth habit, lodging resistance, plant height, shattering resistance, etc.

In addition to phenotypic observations, the genotype of a plant can also be examined. There are many laboratory-based techniques available for the analysis, comparison and characterization of plant genotype; among these are isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The cultivar of the present invention has shown uniformity and stability for all traits, as described in the following cultivar description information. It has been self-pollinated a sufficient number of generations, with careful attention to uniformity of plant type to ensure homozygosity and phenotypic stability. The cultivar has been increased with continued observation for uniformity. No variant traits have been observed or are expected in the new 44A89 cultivar as described in detail hereafter.

Cultivar 44A89 demonstrates excellent yield and superior lodging resistance. 44A89 also exhibits high seed oil and protein percentages. Cultivar 44A89 is a spring canola variety and is specially adapted for Western Canadian canola growing conditions. Morphological Since canola cultivar 44A89 is substantially homogeneous, it can be reproduced by planting seeds of such cultivar, growing the resulting canola plants under self-pollinating or sib-pollinating conditions with adequate isolation, and harvesting the resulting seed using conventional agronomic practices.

TABLE 1

VARIETY DESCRIPTION INFORMATION
44A89

1. Species: *Brassica napus*
2. Type: Spring
3. Plant Height:
   102.0 cm Tall
   10.0 cm shorter than Excel
   Height same as Legend
   Height Class: 2 - medium short
4. Stem Anthocyanin: N/A
5. Seed Cotyledons: medium
6. Seedling Growth Habit (leaf rosette): upright to prostrate
7. Leaves:
   Margins: weak
   Lobing: medium
   Leaf Attachment to stem: partial clasping
   Color: medium green
   Glaucosity: weak to medium
8. Flowers:
   Flower Buds Location: at tip of apical meristem
   Petal color: yellow
   Anther dotting: N/A
   Flowering class: medium early

TABLE 1-continued

VARIETY DESCRIPTION INFORMATION
44A89

9. Pods:
   Pod type: bilateral single pod
   Silique beak length: medium
   Pod length: medium
   Pod width: narrow to medium
   Pod habit: horizonal to semi-erect
   Pedicel length: short
   Ripening class: very early
   Days to maturity: 101.1
   4.8 days earlier than Excel
10. Seeds:
    Unsized seed: 4.03 g/1000
    .60 g less than Cyclone
    Weight class: 4.0–5.0 g
    Seeds per pod: N/A
    Testa color: dark brown to back
11. Chemical composition of seed:
    Erucic acid: low
    Glucosinate content: (based on 9.8 millimoles/g): low
    % Oil: 49.09
    % Protein: 45.32
    Fatty acid composition:
    Palmitic: 3.97
    Stearic: 1.88
    Oleic: 63.4
    Linoleic: 17.2
    Linolenic: 10.0
    Eicosenoic: 1.39
    Erucic: 0.01
12. Frost tolerance: N/A
13. Lodging resistance: strong 14. Herbicide resistance:
    Atrazine: susceptible
15. Disease resistance:
    Sclerotinia Stem Rot: not tested
    Black Leg, Stem Canker: high resistance
    White Rust: high resistance
    Light Leaf Spot: not tested
    Downy Mildew: not tested
    Rhizoctonia Root Rot: not tested
    Alternaria Black Spot: not tested When preparing the detailed phenotypic information that follows, plants of the new 44A89 cultivar were observed while growing using conventional agronomic practices. For comparative purposes canola plants of four publicly available canola cultivars were similarly grown in isolation at the same location and were observed under the same growing conditions.

From review of the table, cultivar 44A89 exhibits short pedicle length, very weak stem anthocyanin coloration and medium cotyledon width which are not seen in any of the other comparison cultivars. Cultivar 44A89 exhibits a plant growth type (semi-protrate to prostrate); leaf glaucousity (weak to medium); leaf lobes (medium; and pod length (short to medium) which are exhibited by only one other of the different cultivars. Cultivar 44A89 clearly possesses a unique combination of morphological traits.

TABLE 2

| MORPHOLOGICAL TRAIT | 44A89 | CYCLONE | EXEL | LEGEND | BULLET |
|---|---|---|---|---|---|
| Canada Type | Spring | Spring | Spring | Spring | Spring |
| Plant Growth Type | semi-prostrate to prostrate | semi-prostrate | semi-prostrate | semi-prostrate to prostrate | semi-prostrate |
| Cotyledon Width | medium | medium to wide | narrow to medium | narrow to medium | medium to wide |
| Leaf Blade Color | medium green | dark green | dark green | medium green | medium green |
| Leaf Attachment to Stem | partial clasping | p[artial clasping | partial clasping | partial clasping | partial clasping |
| Leaf Glaucousity | weak to medium | weak to medium | weak | medium | medium |
| Leaf Lobes | medium | medium strong | medium | weak to medium | strong |
| Leaf Surface | medium | medium to rough | medium | medium | medium |
| Leaf Margin Indentation | weak to medium | medium to strong | weak | weak to medium | weak to medium |
| Stem Anthocyanin Coloration | very weak | weak | medium | medium to strong | weak to medium |
| Seedling Growth Habit | medium | medium | medium | medium | weak to medium |
| Flower Bud Location | buds at tip | buds at tip | buds at tip | buds at tip | buds at tip |
| Flower Petal Coloration | medium yellow | medium yellow | medium yellow | medium yellow | medium yellow |
| Anther Fertility | fertile | fertile | fertile | fertile | fertile |
| Pod Type | bilateral single pod | bilateral single pod | bilateral single pod | bilateral single pod | bilateral single pod |
| Pod Length | short to medium | short | medium | medium | short to medium |
| Pod Width | narrow to medium | narrow | narrow to medium | narrow to medium | medium |
| Pod Beak Length | medium | medium | medium | medium | medium |
| Pedicle Length | short | medium | medium | medium | medium |
| Pod Habit | horizontal to semi-erect | semi-erect | horizontal to semi-erect | semi-erect | horizontal to semi-erect |

INDUSTRIAL APPLICABILITY

This invention also is directed to methods for producing a canola plant by crossing a first parent canola plant with a second parent canola plant wherein the first or second parent canola plant is an inbred canola plant of the new 44A89 cultivar. Further, both first and second parent canola plants can come from the new 44A89 cultivar. Thus, any such methods using the new 44A89 cultivar as a parent are within the scope of the present invention. Advantageously, the canola cultivar of the present invention can be used in crosses with other, different, *Brassica napus* canola inbreds to produce first generation ($F_1$) canola hybrid seeds and plants with superior characteristics.

As used herein, the term "plant" includes plant cells, plant protoplasts, plant cell tissue cultures from which canola plants can be regenerated, such as plant calli, plant clumps, and plant cells that are intact in plants or parts of plants, including embryos, pollen, ovules, flowers, pods, leaves, roots, root tips, anthers, stalks, and the like.

Further production of the 44A89 cultivar can occur by self-pollination or by tissue culture and regeneration. Tissue culture of various tissues of canola and regeneration of plants therefrom is known. For example, the propagation of a canola cultivar by tissue culture is described in any of the following which are hereby incorporated in their entirety by reference: Chuong et al., "A Simple Culture Method for Brassica hypocotyl Protoplasts", *Plant Cell Reports* 4:4–6 (1985); Barsby, T. L., et al., "A Rapid and Efficient Alternative Procedure for the Regeneration of Plants from Hypocotyl Protoplasts of *Brassica napus*", *Plant Cell Reports*, (Spring 1996); Kartha, K. et al., "In vitro Plant Formation from Stem Explants of Rape", *Physiol. Plant,* 31:217–220 (1974); Narasimhulu, S., et al., "Species Specific Shoot Regeneration Response of Cotyledonary Explants of Brassicas", *Plant Cell Reports*, (Spring 1988); Swanson, E., "Microspore Culture in Brassica", *Methods in Molecular Biology*, Vol. 6, Chapter 17, p. 159 (1990).

The seed of the 44A89 cultivar, the plant produced from such seed, the hybrid canola plant produced from the crossing of the 44A89 cultivar, the resulting hybrid seed, and various parts of the hybrid canola plant can be utilized in the production of an edible vegetable oil or other food products in accordance with known techniques. The remaining solid meal component derived from seeds can be used as a nutritious livestock feed.

Performance Examples of the 44A89 Cultivar

Performance data for the new 44A89 cultivar is presented hereafter.

Table 3 compares the agronomic traits of 44A89 to the same reference varieties earlier compared for morphological traits, namely Cyclone, Exel, Legend and Bullet.

TABLE 3

| Trait | No. of Yr. | No. of Loc. | LDS 0.05 | 44A89 | CYCLONE | EXEL | LEGEND | BULLET |
|---|---|---|---|---|---|---|---|---|
| Yield (q/ha) | 2 | 29 | 1.08 | 30.7 | 27.92 | 26.81 | 28.18 | 27.25 |
| Plant Height (cm) | 2 | 26 | 2.29 | 102 | 109 | 112 | 102 | 113 |
| Days to flowering (days) | 2 | 24 | 0.42 | 47 | 48.2 | 48.8 | 47.1 | 48 |
| Days to maturity (days) | 2 | 27 | 0.63 | 101.1 | 105.6 | 105.9 | 104.3 | 104.9 |
| Resistant to lodging # | 2 | 16 | 0.39 | 6.9 | 6.1 | 6.3 | 5.0 | 5.6 |
| Seed Oil % | 2 | 30 | 0.33 | 49.09 | 46.45 | 48.69 | 47.34 | 47.83 |
| Seed Protein % | 2 | 30 | 0.68 | 45.32 | 44.46 | 44.14 | 45.07 | 43.78 |
| Glucosinolate (Umol/g) | 2 | 28 | | 9.8 | 10.7 | 11.7 | 15.3 | — |
| Chlorophyll content (ppm) | 1 | 4 | | 13.9 | 61.1 | 38.7 | 33.1 | — |
| 1000 seed weight (g) | 2 | 29 | 0.04 | 4.03 | 4.63 | 3.88 | 4.17 | 3.85 |
| Blackleg Reaction # | 2 | 4 | 0.41 | 8.04 | 6.72 | 5.49 | 6.15 | 6.88 |

As can be seen from the table, cultivar 44A89 is superior in yield, lodging resistance, seed oil content, seed protein content, and back leg reaction number than each of the reference varieties. 44A89 also demonstrates a unique chlorophyl content of 13.9 parts per million which is significantly lower than all of the reference varieties. 44A89 is earlier to mature than all of the comparison varieties as well. Cultivar 44A89 clearly demonstrates a unique combination of agronomic traits.

DEPOSITS

Applicant has made a deposit of at least 2500 seeds of Canola Cultivar 44A89 with the American Type Culture Collection (ATCC), Manassas, VA 20110 USA, ATCC Deposit No. PTA-3289. The seeds deposited with the ATCC on Apr. 13, 2001 were taken from the deposit maintained by Pioneer Hi-Bred International, Inc., 800 Capital Square, 400 Locust Street, Des Moines, Iowa 50309-2340 since prior to the filing data of this application. This deposit of the Canila Cultivar 44A89 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801 - 1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of his rights granted under this patent or under the Plant Variety Protection Act (7 USC 2321 et seq.). U.S. Plant Variety Protection of Canola Cultivar 44A89 has been applied for under Application No. 9800045.

The foregoing invention has been described in detail by way of illustration and example for purposes of exemplification. However, it will be apparent that changes and modifications such as single gene modifications and mutations, somaclonal variants, variant individuals selected from populations of the plants of the instant cultivar, and the like, likewise are considered to be within the scope of the present invention.

What is claimed is:

1. A canola seed designated 44A89 having been deposited under ATCC Accession No. PTA-3289.

2. A canola plant, or parts thereof, produced from the seed of claim 1.

3. Pollen of the plant of claim 2.

4. An ovule of the plant of claim 2.

5. A canola plant, or parts thereof, having all the physiological and morphological characteristics of the plant of claim 2.

6. A tissue culture of regenerable cells of the plant of claim 2.

7. A tissue culture according to claim 6, the cells or protoplasts being of a tissue selected from the group consisting of leaves, pollen, embryos, roots, root tips, pods, flowers, ovules, and stalks.

8. A canola plant regenerated from the tissue culture of claim 6, capable of expressing all the morphological and physiological characteristics of the 44A89 cultivar, the seed of which has been deposited under ATCC Accession No. PTA-3289.

9. A canola plant having all of the physiological and morphological characteristics of the canola plant of claim 2, said canola plant having been produced by a tissue culture process using the canola plant of claim 2 as the starting material.

10. A method for producing a first generation ($F_1$) hybrid canola seed comprising crossing the plant of claim 2 with a different inbred parent canola plant and harvesting the resultant first generation ($F_1$) hybrid canola seed.

11. The method of claim 10 wherein the inbred canola plant or parts thereof produced from the seed designated 44A89 having been deposited under ATCC accession number is the female parent.

12. The method of claim 10 wherein the inbred canola plant or parts thereof produced from the seed designated 44A89 having been deposited under ATCC accession number is the male parent.

\* \* \* \* \*